United States Patent [19]

Pell et al.

[11] Patent Number: 4,850,348
[45] Date of Patent: Jul. 25, 1989

[54] ENDOTRACHEAL TUBE APPARATUS AND METHOD

[76] Inventors: Donald M. Pell, P.O. Box 31647, St. Petersburg, Fla. 33732-1647; Cosimo Martinetto, 5613 Half Moon Lake Dr., Tampa, Fla. 33625

[21] Appl. No.: 9,280

[22] Filed: Jan. 30, 1987

Related U.S. Application Data

[63] Continuation-in-part of Ser. No. 693,891, Jan. 23, 1985, abandoned, and a continuation-in-part of Ser. No. 748,446, Jun. 25, 1985, abandoned, and Ser. No. 771,819, Sep. 3, 1985, abandoned.

[51] Int. Cl.$^4$ .............................................. A61M 16/00
[52] U.S. Cl. .......................... 128/207.15; 128/207.17; 604/96; 604/100; 604/280
[58] Field of Search ...................... 128/200.26, 207.14, 128/207.15, 207.18, 100; 604/93, 96–99, 101, 103, 280

[56] References Cited

U.S. PATENT DOCUMENTS

| | | | |
|---|---|---|---|
| 2,842,458 | 6/1959 | Auzin | 604/96 |
| 3,833,004 | 9/1974 | Vazquez et al. | 604/100 |
| 3,866,599 | 2/1975 | Johnson | 604/96 |
| 3,890,976 | 6/1975 | Bazell et al. | 128/207.15 |
| 4,147,169 | 4/1979 | Taylor | 604/100 |
| 4,419,095 | 12/1983 | Nebergall et al. | 128/207.15 |
| 4,430,076 | 2/1984 | Harris | 604/96 |
| 4,469,483 | 9/1984 | Becker et al. | 604/280 |
| 4,502,482 | 3/1985 | DeLuccia | 128/207.18 |
| 4,584,998 | 4/1986 | McGrail | 128/207.15 |
| 4,637,388 | 1/1987 | Melendy | 128/207.15 |

OTHER PUBLICATIONS

"Tubing Size Comparison Chart", Foregger catalogue, 1975.

*Primary Examiner*—Max Hindenburg
*Assistant Examiner*—K. M. Reichle
*Attorney, Agent, or Firm*—Bacon & Thomas

[57] ABSTRACT

Endotracheal apparatus including an endotracheal tube having unique physical characteristics so that it will not kink or collapse during intubation or while in place. A novel cuff or balloon is on the distal end region of the tube to accurately center the tube end in the trachea without danger that the open distal end of the tube will contact the trachea wall, and to permit the minimum length tube to be used. A novel bite piece and retainer is used to secure the tube in the patient's mouth with optimum comfort.

5 Claims, 3 Drawing Sheets

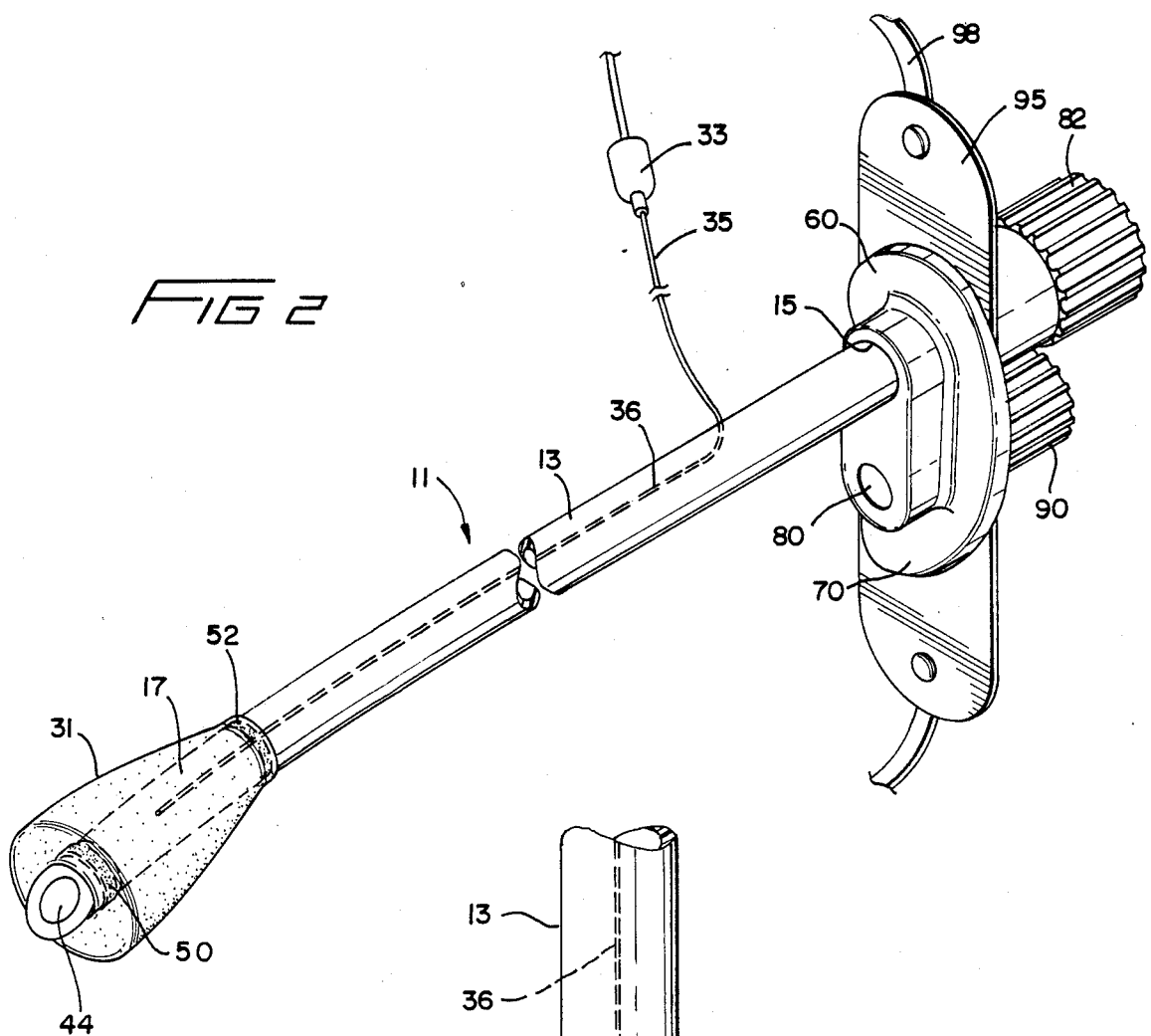
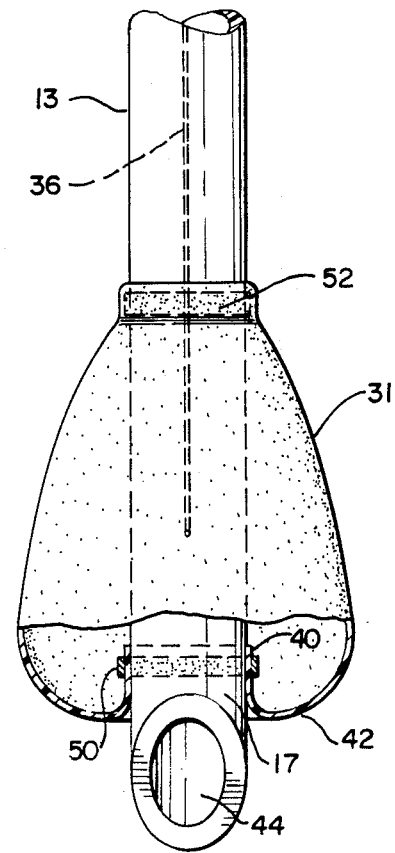

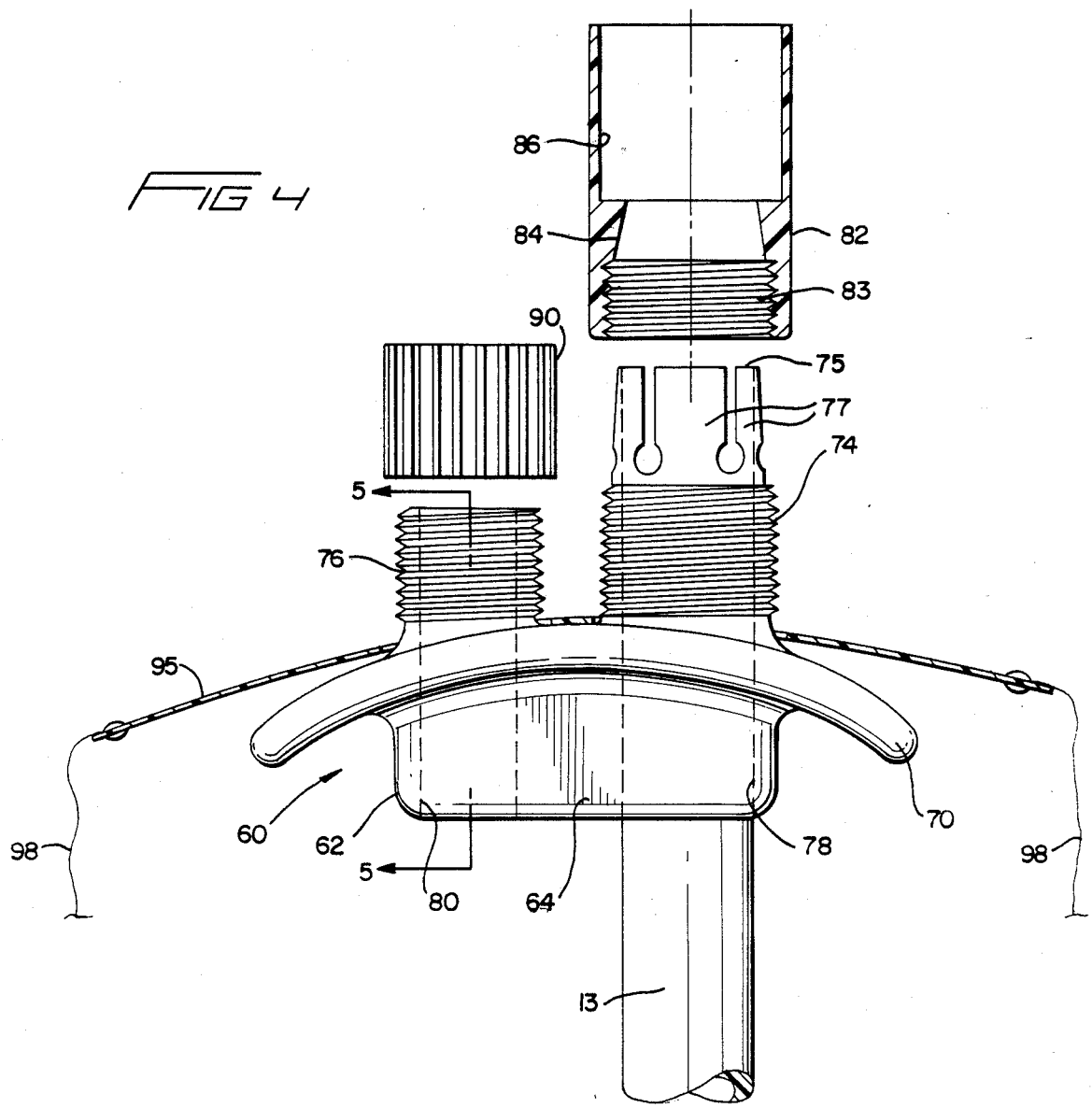
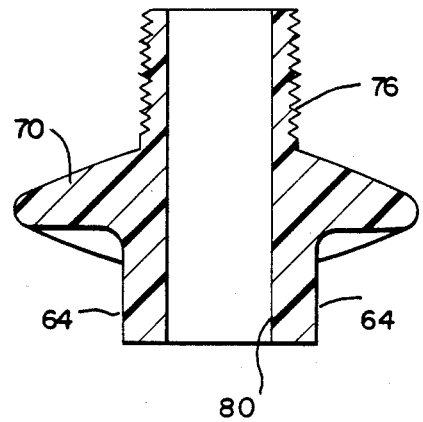

ENDOTRACHEAL TUBE APPARATUS AND METHOD

This application is a continuation-in-part of our applications Ser. Nos. 693,891, filed Jan. 23, 1985; 748,446, filed June 25, 1985; and 771,819, filed Sept. 3, 1985, all now abandoned.

BACKGROUND OF THE INVENTION

There are many types of endotracheal tubes known to the medical profession, and many types of known apparatus intended to keep the tubes in place in the patient's oral cavity and trachea. We have found that the apparatus that currently is available have deficiencies that not only cause discomfort to the patient, but also have life threatening consequences. Sustained lateral and/or axial movement of a tracheal tube results in irritation, and possibly ulceration, of the lips, tongue, and trachea, including the vocal cords of the patient.

Oral bite pieces that engage the endrotracheal tube have been provided in an attempt to hold the tube in a fixed position in the patient's mouth and to prevent the patient from biting the tube and blocking or severing it. The bite pieces are ill-fitting and cause extreme discomfort to many patients.

Of even more serious consequences are the deficiencies of the materials selected for use in manufacturing the tubing. Some of the plastic materials used for making endrotracheal tubing are not heat stable in their physical characteristics at body temperatures and do not remain firm enough at those temperatures to retain their desired shapes while being inserted, and while in place. Sometimes a tube will collapse and/or kink, causing irritation if left in place, and more importantly, significantly reducing the rate of flow of air, oxygen mixture, etc., that can flow through the tube. The total volume of fluid flow per unit of time through a tube is given by Poiseuille's law as follows.

$$\frac{dV}{dt} = \frac{\pi}{8} \frac{R^4}{n} \frac{(p_1 - p_2)}{L}, \text{ where}$$

V = volume of flow.
R = radius of the tube.
$p_1$ and $p_2$ are the pressures at the respective ends of the tube.
n = viscosity of the flowing fluid.
L = the length of the tube.

From this equation it is seen that any slight restriction in the radius R of the tube can have a significant reduction in the rate of flow through the tube since the radius is raised to the fourth power.

Additionally, it is seen that the rate of flow is inversely proportional to the length of the tube. Therefore, for a weak patient who does not have the strength to overcome any significant resistance to breathing, not only must the tube remain uniform in cross section throughout its length, but the tube must be as short as possible. These basic physical considerations seem not to have been previously taken into consideration in the construction and method of administering the intubation of endotracheal tubes.

SUMMARY OF THE INVENTION

My invention takes optimum advantage of the basic physical considerations discussed above to reduce as much as possible the resistance to breathing a patient experiences when a tracheal tube is positioned in his trachea. The material from which the tube is made is stable in its physical characteristics at body temperatures and will not collapse or kink under conditions to be experienced in use. Contributing to the maintenance of the cross sectional shape of the tube is a judicious selection of wall thickness relative to the tube diameter with a diameter to wall thickness ratio in the range of 3 to 4:1 to permit the tube to readily bend through at least 90 degrees without the wall collapsing. To assure that the tube is of minimum possible length, the deflated cuff or balloon at the distal end of the tube is positioned in the trachea just below the vocal cords. The tube then is inflated and passed through and secured in an oral bite piece. The excess length of tubing that extends beyond the bite piece then is severed. This procedure assures that the tube is as short as it can be made without irritating or damaging the vocal cords, thereby providing the minimum value of L for the above equation. Other advantages will be discussed below.

As mentioned, it is desirable to secure the endotracheal tube in place to prevent it from moving laterally or axially. To accomplish this we provide an improved oral bite piece that is relatively small in size, comfortably will fit a majority of patients, and provides means for inserting a suction tube or surgical tool into the patient's trachea. The bite piece is made of material that is yielding enough to be comfortable for the patient, and is rigid enough to protect the tube from being restricted or severed by the patient's dental arches, even in case of a seizure by the patient. The bite piece may be rotated in the patient's oral cavity to move the endotracheal tube to the opposite side thereof to relieve irritation and prevent ulceration.

BRIEF DESCRIPTION OF THE DRAWINGS

The invention will be described by referring to the accompanying drawings wherein:

FIG. 2 is a more detailed illustration of the tube and bite piece of FIG. 1;

FIG. 3 is a simplified illustration of the distal end of the endotracheal tube of this invention;

FIGS. 4 and 5 are more detailed illustrations of the bite piece of FIG. 1.

DESCRIPTION OF PREFERRED EMBODIMENT

Figure 1:
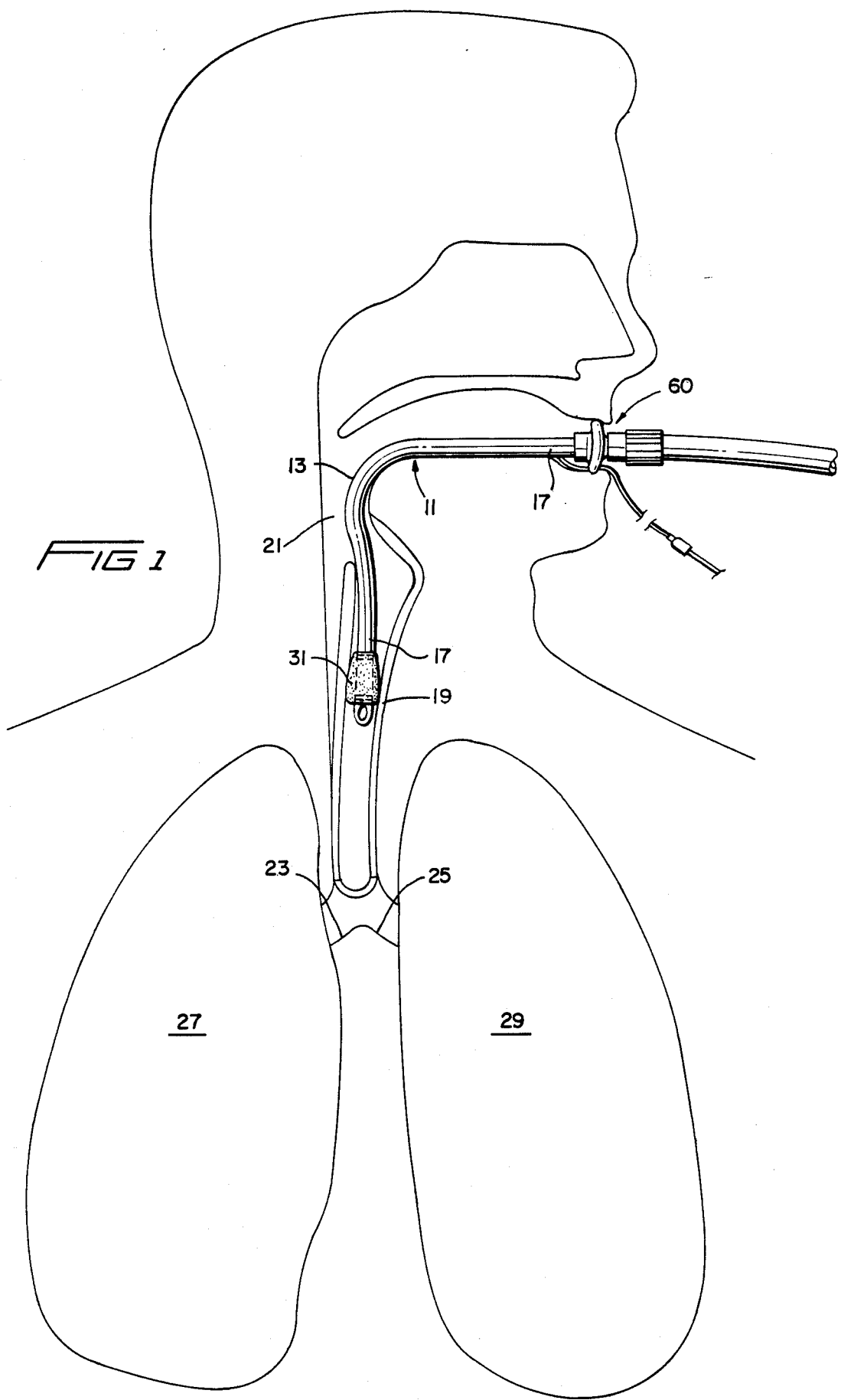
FIG. 1 is a simplified illustration of the endotracheal tube of this invention positioned in a human patient in accordance with the teachings of the invention and with the proximal end secured in our novel oral bite piece.

The presently preferred embodiment of endotracheal tube is illustrated in FIGS. 1 and 2 and is designated by the numeral 11. The endotracheal tube 11 includes a length of tubing 13 having a distal end portion adapted to be orally intubated in a patient's trachea and the proximal end portion adapted to protrude from the patient's mouth. The tubing is sufficiently flexible to bend and conform to the patient's anatomy, but has the properties to prevent kinking and collapsing during insertion and while in place, as will be discussed below. As seen in FIG. 1, this means that tube 13 must be able to bend through substantially 90 degrees without the wall collapsing or kinking. The presently preferred tubing is made from a medical grade silicone plastic material selected so that the tube is stable in its physical characteristics at human body temperature to be encountered in use, and has a hardness in the range of about 80 durometer. In one size of tubing made for oral intubation, the inner diameter was 0.32 inch (8 mm), and the wall thickness was 0.100 inch (2.5 mm). These dimensions are not critical, but are representative.

A presently preferred composition of silicone had the following constituent materials, and approximate proportions by weight.

Dimethyl silicone: 90%
Inert silica filler: 10%
Platinum salts as catalyst or curing agent: less than 1%

Conventional mixing, extrusion and curing methods may be used and are well known to those skilled in the art.

Although the above described silicone material is presently preferred, other materials having the described characteristics may be used. For example, a medical grade, biocompatible polyurethane material may be used. The same dimensions and hardness given above will be used.

Tube 13 is of one-piece, extruded construction and has smooth exterior and interior surfaces throughout. As best seen in FIGS. 2 and 3, the distal end of the tube 13 usually is cut diagonally, i.e., at an acute angle to the central axis of the tube. As illustrated in FIG. 1, the tube is flexible and conforms to the patient's anatomy when inserted. It is a characteristic of the tube of this invention that it will not kink or collapse while being intubated or after being in place for great lengths of time.

The distal portion 17 of the endotracheal tube is provided with an expandable cuff or balloon 31 of a gas impervious material such as a thin sheet of silicone material of the type described above. Cuff 31 is inflated by means of a pilot balloon 33 connected to the cuff by an external tube 35 and internal passage 36 in the wall of tube 13, as is known in the art. See FIG. 2. When the cuff 31 is inflated to engage the wall of trachea 19, air or other gases pass to and from a patient's lungs, 27, 29, through the bronchi 23, 25 and through the interior of the tube 13. The proximal end 15 of the tube 13 is adapted to be connected to a ventilator or oxygen source and/or a suction device in a manner described below.

Some important features of the cuff and its construction and arrangement on the distal end of the tube 13 now will be discussed by referring to FIG. 3. The distal end of the cuff 31 has an annular end 40 that is secured in contact with the tube and faces in the direction of the proximal end of the tube. The material of the cuff extends toward the distal end of the tube, then reverses its direction to overlap the annular end 40 and extends to the proximal end of the cuff. The material at the proximal end of the cuff does not reverse direction. Both ends of the cuff are secured to the outer surface of the tube by silicone cement, or some other suitable means.

It will be seen that the distal end 42 of the cuff is as close as possible to the open end 44 of the tube without interfering with that opening. The reason for this is that the cuff may be inserted within the trachea just below the vocal cords and then inflated, and the end of the tube then does not extend much beyond this region. This is in keeping with the objective of making the length L in the above equation as short as possible to get as much air as possible through the tube with a given amount of effort on the part of the patient.

The material of the cuff is folded under on the distal end to provide the greatest diameter of the inflated cuff closest to the open end 44 of the tube. This provides for optimum centering of that open end within the trachea and minimizes the chance that the open end 44 will come into contact with the trachea wall and become wholly or partially blocked by that wall. In the prior art endotracheal tubes where the cuff is located some distance away from the open end of the tube, it has happened that the open end came to rest against the trachea wall and became blocked. A further deleterious feature of the described prior art arrangement is that the tube extends further down into the trachea and unnecessarily increases the length L.

Another advantage that is gained by assuring that the tube 13 is short in length and the open end 44 is positioned just below the vocal cords is that the diagonal tip of the tube is relatively far removed from the bronchi so that positive or negative pressure applied from the tube is more likely to affect both bronchi and lungs equally. If the diagonal tip of tube 13 within the carina gets too close to the proximal ends of the bronchi and is not exactly symmetrically positioned with respect to both of them, an unequal suction bias, for example, might be created on the two bronchial tubes. Also, with the situation just described, the lungs might receive unequal oxygen inputs from an external source, and might experience unequal $CO_2$ exchange as a result of the tip of the tube migrating into one of the bronchia. When the open end 44 of tube 13 is farther removed from the bronchi, positive and negative pressures are more likely to be substantially equal at the two bronchi since the diagonal tube end will have less of a blocking effect and balanced secretion removal will be achieved.

As seen FIG. 3, respective bands of radiopaque material 50 and 52 are at or adjacent the respective ends of the cuff 31 to mark the opposite end regions thereof. These will assist in locating the position of the cuff in the trachea when viewing an x-ray picture of the intubated endotracheal tube. The radiopaque bands may be made of any of the known materials that are used for this purpose. Bismuth trioxide and tungsten barium compounds for example have been used for this purpose. They may be applied in the form of a paint or paste, or may be solid bands that are crimped in place. Desirably, thin beads or films of suitable silicone cement are run about the outer surfaces of the bands 50 and 52.

The proximal end of endotracheal tube 13 passes through and is secured in an oral bite piece 60 that is seen most clearly in FIGS. 4 and 5. The shaped end 62 is received in the patient's mouth and the patient's dental arches engage the lateral surfaces 64 on opposite sides of the piece. Shaped end 62 curves upwardly to join curved lip guard 70 which is accurately shaped transversely according to a dentally correct curve so that shaped end 62 substantially conforms to the curve of the front four teeth on the top and bottom dental arches of a majority of the population. Since the complete dental arches of the patient are not required to engage and conform to the shaped end of the bite piece, the possibility is greater that a comfortable fit will be achieved.

Bite piece 60 is molded of a suitable nontoxic material such as the above described silicone that is somewhat yieldable, is comfortable for the patient, and yet is stiff enough to support and protect the tube.

The proximal, or exterior, side of bite pieces 60 has two integral, externally threaded hollow studs or collets 74 and 76 thereon which extend outwardly from the bite piece. Collets 74 and 76 are molded of the same material as the remainder of the bite piece. Parallel smooth bore apertures 78 and 80 pass completely through bite piece 60 and are in registration with, or extend through, the hollow interiors of the respective threaded studs 74 and 76. Endotracheal tube 13 is received in aperture 78 and extends to the outer end 75 of collet 74.

As clearly seen in FIG. 4, the proximal end region 75 of hollow stud 74 is slotted so as to provide flexible finger-like members 77 at the end thereof. An interially threaded adapter-connector 82 has a threaded region 83 that engages the threads on collet 74, and a smooth bore section 84 that has a decreasing diameter so that when adapter-connector 82 is threaded into engagement with collet 74 the reduced diameter section 84 engages the flexible fingers 77 and forces them inwardly to securely engage the outer surface of the tube 13 that has been passes through the bore 78 in bite piece 60. The force applied by the flexible fingers is sufficient to hold the tube securely in the bite piece, but the silicone material of the outer surface is soft enough that the cross sectional area of the tube is not restricted or reduced. This clamping action securely holds the tube in place and reduces the possibility of irritation to the patient's, lips, tongue, vocal cords, and trachea. Other types of compression fittings may be used in keeping with the requirements stated herein.

The top end of adapter connector 82 has a large diameter bore therein in communication with the tapered bore section 84 and threaded section 83, and is adapted to receive mating connector pieces for connecting the endotracheal tube to external apparatus such as an oxygen source, or a suction source and apparatus for example. Because collet 74 and its flexible fingers 77 are engaged by adapter-connector 82 exterior to tube 13, the tube is securely held without reducing the radius R of the tube. As seen from the above equation, flow through the tube is not reduced as it would be if the adapter-connector were inserted within the end of tube 13 to thereby reduce the radius of the tube by the wall thickness of the adapter-connector.

An internally threaded, closed-end cap 90 is adapted to engage the threads of collet 76 to close the bore or passageway 80 through bite piece 60 when that passageway is not in use. As is known, this second passageway 80 is used for the intubation of additional instruments or tubing without disturbing endotracheal tube 13.

By providing just two passageways through the bite piece 60 it can be of a relatively small size, and together with its dentally correct shape that engages only the front positions of the dental arches, optimum comfort is provided for the patient.

A thin, flexible sheet of plastic material 95 is employed as a retainer member to hold bite piece 60 in the patient's mouth. A pair of apertures in retainer member 95 pass over collets 74, 76 and permit the retainer member to rest on the high portion of the bite pieces at the central region thereof. When adapter-connector 82 and cap 90 are fully threaded onto their respective collets they hold retainer member 95 in place on bite piece 60. An elastic headband 98 passes around the patient's head to hold the retainer and bite piece in place. Because retaining member 95 is thin and flexible, and because headband 98 is stretchable, bite piece 60 is not forced hard against the lips and dental arches of the patient, and may permit some slight motion in the patient's mouth without the exertion of a significant force by the patient. This contributes to the comfort of the patient without allowing the tube to be loose in the patient's mouth and trachea.

In the use of the apparatus described above, the physician inserts a laryngoscope through the mouth and into the larynx of the patient in the customary manner for a procedure of this type. He then inserts the endotracheal tube through the laryngoscope and intubates the tube into the trachea until the cuff 31 is sufficiently below the vocal cords to assure that the inflated cuff will not contact them. The cuff then is inflated by means of balloon 33 and small tubing 35. With the proximal end of the endotracheal tube extending outwardly from the oral cavity, the end of the tube is passed through bore 78 and collet 74 of bite piece 60 and the bite piece is positioned in the patient's mouth. After making sure that the tube is properly positioned in the trachea and is free of kinks and undesired bends, the proximal end of the tube is cut off substantially flush with the outer end 75 of collet 74. The exterior fitting adapter connector 82 then is screwed onto collet 74 to the full extent of the threads. As explained, this causes the flexible fingers 77 on collet 74 to be urged inwardly by the tapered section 84 of the adapter-connector to secure tube 13 in the bite piece. Elastic headband 98 then is passed about the patient's head to hold the assembly in place with a minimum of discomfort to the patient.

The position of endotracheal tube 13 may be shifted in the patient's mouth to minimize irritation to the lips and tongue, for example, by unscrewing adapter-connector 82 so that flexible fingers 77 on collet 74 no longer bind tube 13. The physician or attendant then holds the tube on the distal side of bite piece 60 and pulls the bite piece from the patient's mouth. The bite piece then is rotated 180 degrees about tube 13 so that the positions of collets 74 and 76 are reversed from their previous positions. Bite piece 60 then is slid inwardly on tube 13 until it again is firmly in place in the patient's mouth. Tube 13 now will be on the opposite side of the patient's mouth. Adapter-connector 82 then is rethreaded on collet 74 so that flexible fingers 77 again engage the outer surface of the tube. During this procedure, it may be necessary to remove headband 98 from the patient's head. The above-described procedure is simple and causes a minimum of discomfort to the patient.

The position of cuff 31 in the tracea may be checked anytime subsequent to intubation by taking an x-ray picture of the throat region of the patient and viewing the radiopaque markers 50 and 52 on the picture. As previously stated, the cuff should be as close to the vocal cords as possible without causing irritation to the them in order to keep the length L of the tube as short as possible.

From the above description it is evident that the apparatus and method of this invention not only are safer on the patient's tissues, but greatly reduce the patient's work of breathing, and thus serve to relieve more quickly his dependency on such apparatus.

While a preferred embodiment of the invention has been illustrated and described, it is to be understood that alterations and modifications may be made to the described embodiment without departing from the scope of the present invention.

I claim:
1. An endotracheal tube comprising
   a flexible member having distal and proximal open ends and a tubular passage therebetween, said member being formed of nontoxic material that is heat stable in its physical characteristics within the range of human temperature to be encountered in use, has a hardness of about 80 durometer, and an inside diameter to wall thickness ratio in the range of 3 to 4:1 so that the member is non-collapsible during insertion and while in place in the trachea, and is capable of withstanding a 90 degree bend without collapsing, and further including an inflatable cuff or balloon of a gas impervious material on the distal end of said tube, said cuff having distal and proximal ends secured to the exterior surface of the tube, said distal end of the cuff comprising an annular cuff end having an opening facing in the direction of the proximal end of the tube, the material of the cuff extending toward the distal end of the tube and reversing its direction to overlap said open end of the cuff and then extending to the proximal end thereof, and said proximal end of the cuff comprising an annular cuff end having an opening facing in the direction of the proximal end of the tube, said cuff tapering in diameter from said distal end to said proximal end, said cuff at the distal end of the cuff being positioned at the distal end of the tube substantially at the open end thereof, but free of that opening, and means for inflating said cuff on said tube.

2. The endotracheal tube claimed in claim 1 wherein the distal end of said tube is inclined to the central axis of the tube.

3. The endotracheal tube claimed in claim 2 wherein the respective ends of the cuff includes, respective markers of a radiopaque material disposed thereon and thereby defining, the end regions of the cuff.

4. The combination claimed in claim 3 wherein the radiopaque material on the distal end of said cuff is positioned under the outer layer of said material and over the one thickness of said material that is adjacent said tube.

5. The endotracheal tube claimed in claim 1 wherein said material is a silicone material having the following approximate composition: 90 percent by weight of dimethyl silicone; 10 percent by weight of an inert silica filler; and less than 1 percent of a platinum salt catalyst.

* * * * *